United States Patent
Vilsmeier et al.

(10) Patent No.: US 10,769,240 B2
(45) Date of Patent: Sep. 8, 2020

(54) DETERMINING MEDICAL OUTCOME QUALITY

(71) Applicant: Brainlab AG, Munich (DE)

(72) Inventors: Stefan Vilsmeier, Munich (DE); Bálint Varkuti, Munich (DE)

(73) Assignee: BRAINLAB AG, Munich (DE)

( * ) Notice: Subject to any disclaimer, the term of this patent is extended or adjusted under 35 U.S.C. 154(b) by 967 days.

(21) Appl. No.: 15/311,833

(22) PCT Filed: Apr. 30, 2015

(86) PCT No.: PCT/EP2015/059448
§ 371 (c)(1),
(2) Date: Nov. 16, 2016

(87) PCT Pub. No.: WO2015/173028
PCT Pub. Date: Nov. 19, 2015

(65) Prior Publication Data
US 2017/0103173 A1    Apr. 13, 2017

Related U.S. Application Data

(63) Continuation of application No. PCT/EP2014/001330, filed on May 16, 2014.

(51) Int. Cl.
G06Q 10/00    (2012.01)
G06Q 50/00    (2012.01)
(Continued)

(52) U.S. Cl.
CPC .......... G06F 19/321 (2013.01); G06F 19/324 (2013.01); G06F 19/325 (2013.01);
(Continued)

(58) Field of Classification Search
CPC ...... G06F 19/00; G06F 19/321; G06F 19/325; G06F 19/3481; G06F 17/5009;
(Continued)

(56) References Cited

U.S. PATENT DOCUMENTS

2004/0153128 A1* 8/2004 Suresh ................ G06F 19/3481
607/14
2006/0248031 A1* 11/2006 Kates ..................... G16H 50/20
706/25
(Continued)

FOREIGN PATENT DOCUMENTS

EP         2575067      4/2013
WO       2004040437     5/2004
WO       2013075127     5/2013

OTHER PUBLICATIONS

European Patent Office, International Search Report and Written Opinion of PCT/EP2015/059448 dated Jul. 8, 2015.
(Continued)

Primary Examiner — Trang T Nguyen
(74) Attorney, Agent, or Firm — Middleton Reutlinger (57) ABSTRACT

The present invention relates to a medical data processing method of determining an outcome quality of a medical procedure, the method comprising the following steps which are constituted to be executed by a computer: a) acquiring (S1) pre-completion medical image data describing an anatomical structure of a patient's body in a state before the medical procedure has been completed on the anatomical structure, the anatomical structure being subject to the medical procedure; b) acquiring (S1) pre-completion non-image medical data describing a state and medical history of the patient before the medical procedure has been completed on the anatomical structure; c) acquiring (S2) medical procedure planning data describing a plan for execution of the medical procedure to be carried out on the anatomical structure; d) determining (S2), based on the pre-completion medical image data and the medical procedure planning data, procedure application describing an application of the medical procedure planning data to the pre-completion medical image data; e) acquiring (S5) post-completion non-
(Continued)

image medical data describing a state and medical history of the patient after the medical procedure has been completed on the anatomical structure; f) acquiring (S5) post-completion medical image data describing the anatomical structure in a state after the medical procedure has been completed on the anatomical structure; g) determining (S6, S7), based on the procedure application data and the pre-completion non-image medical data and the post-completion non-image medical data and the post-completion medical image data, outcome quality data comprising a quality measure describing a quality of the outcome of the medical procedure, the quality measure for example being specific to the indication in question, properties of the patient and the executive medical entity.

9 Claims, 1 Drawing Sheet (51) Int. Cl.
- *G06F 19/00* (2018.01)
- *G16H 50/70* (2018.01)
- *G16H 50/20* (2018.01)
- *G16H 40/63* (2018.01)

(52) U.S. Cl.
CPC ............. *G16H 40/63* (2018.01); *G16H 50/20* (2018.01); *G16H 50/70* (2018.01)

(58) Field of Classification Search
CPC .............. G06F 19/3418; G06F 3/0482; G06F 3/04842; G06F 3/04847; G06F 3/016; G06F 17/50; G06F 19/324; G06F 3/0321; G16H 50/50; G16H 50/20; G16H 40/63; G16H 50/70; G16H 10/20; G16H 40/20; G16H 40/40; G16H 30/20; G16H 20/40; G16H 30/40; G16H 40/60; G16H 40/67; G06Q 10/00; G06Q 10/10; G06Q 50/24; G06Q 20/1085; G06Q 20/042; G06Q 20/3223; G06Q 20/409; G06Q 10/1095; G06Q 20/3221

See application file for complete search history.

(56) References Cited

U.S. PATENT DOCUMENTS

| | | | |
|---|---|---|---|
| 2010/0174557 A1* | 7/2010 | Bundschus | G06Q 10/00 705/3 |
| 2015/0057646 A1* | 2/2015 | Aljuri | A61B 1/307 606/10 |
| 2015/0169827 A1* | 6/2015 | LaBorde | H04L 67/12 705/51 |
| 2015/0254838 A1* | 9/2015 | Blumhofer | G06T 7/0012 382/131 |
| 2015/0261922 A1* | 9/2015 | Nawana | G16Z 99/00 702/19 |

OTHER PUBLICATIONS

Wang, Shanshan, et al., "An Automated DICOM Database Capable of Arbitrary Data Mining (Including Radiation Dose Indicators) for Quality Monitoring", Journal of Digital Imaging, vol. 24, No. 2 Sep. 8, 2010.

* cited by examiner

DETERMINING MEDICAL OUTCOME QUALITY

The present invention is directed to a data processing method of determining an outcome quality of a medical procedure based on in particular computerized processing of medical image data and non-image medical data.

For the assessment of the quality of a medical procedure planning (defining a planned medical procedure) in view of the results achieved by applying the planned medical procedure (i.e. its outcome), it is desirable to include additional information which may influence the outcome of the medical procedure.

In general, the outcome of specific medical procedures such as open surgery or radiotherapy can be determined by comparing medical image data taken for a specific patient before and after the patient has undergone the medical procedure. However, such information taken by itself may not be enough to judge the quality of the outcome for a plurality of patients and to determine the performance of a medical institution such as a hospital or individual practitioner or the performance of a specific treatment. In particular, a quality of outcome determined on the basis of only medical image data may neglect statistical effects due to differing living habits of the patients or ailments which the patients are suffering from in addition to the pathologic state which shall be treated by applying the medical procedure.

A problem to be solved by the present invention is to provide a method of determining an outcome quality for a medical procedure which allows to validly determine the performance of a medical institution in relation to that medical procedure for in particular a plurality of patients.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

EXEMPLARY SHORT DESCRIPTION OF THE PRESENT INVENTION

In the following, a short description of the specific features of the present invention is given which shall not be understood to limit the invention only to the features or a combination of the features described in this section.

The invention relates to a computer-implemented method of determining the quality of the outcome of a medical procedure (such as surgery or radiotherapy) based on a statistical analysis (in particular comparison) of a treatment plan (which is defined before the medical procedure starts) with medical image data non-image medical data which was taken after the medical procedure has been conducted. The treatment plan is determined based on in particular medical image data which was taken before the medical procedure has been finished, in particular before it is started, and information about the envisaged medical procedure. The quality of the outcome defines in particular at least one of a medical result and an efficiency (advantageously, economic efficiency) of the medical procedure and may serve as a basis for future treatment planning, improvement of the medical procedure or ranking of healthcare institutions and/or healthcare practitioners.

General Description of the Present Invention

In this section, a description of the general, in particular preferred features, of the present invention is given.

In one aspect, the present invention is in a first embodiment directed to a medical data processing method of determining an outcome quality of a medical procedure, the method comprising the following preferred steps which are in particular constituted to be executed by a computer:

a) acquiring pre-completion medical image data describing (in particular defining) an anatomical structure of a patient's body in a state before the medical procedure has been completed on the anatomical structure (in particular, before execution of the medical procedure has started or while it is being executed, but has not been finished yet), the anatomical structure being subject to the medical procedure;

b) acquiring pre-completion non-image medical data describing (in particular defining) a state and medical history of the patient before the medical procedure has been completed on the anatomical structure (in particular, before execution of the medical procedure has started or while it is being executed, but has not been finished yet);

c) acquiring medical procedure planning data describing (in particular defining) a plan for execution of the medical procedure to be carried out on the anatomical structure;

d) determining, based on the pre-completion medical image data and the medical procedure planning data, procedure application data describing (in particular defining) an application of the medical procedure planning data to the pre-completion medical image data;

e) acquiring post-completion non-image medical data describing (in particular defining) a state and medical history of the patient after the medical procedure has been completed on the anatomical structure;

f) acquiring post-completion medical image data describing (in particular defining) the anatomical structure in a state after the medical procedure has been completed on the anatomical structure;

g) determining, based on the procedure application data and the pre-completion non-image medical data and the post-completion non-image medical data and the post-completion medical image data, outcome quality data comprising a quality measure describing (in particular defining) a quality of the outcome of the medical procedure, the quality measure for example being specific to the indication in question, properties of the patient and the executive medical entity.

The pre-completion non-image medical data describes (in particular defines) for example the patient's personal particulars (for example, at least one of his gender, age, ethnicity, height, mass, and place of residence) diagnosis (in particular, his pathological state such as illness or injury which is to be treated by applying the medical procedure, but if applicable also any further pathological states such as a psychic illness, drug-addiction or chronic diseases such as diabetes or rheumatism), his living habits (e.g. whether he is overweight, smokes, consumes alcohol), other personal information (e.g. whether in the case of a female patient she is pregnant or has given birth in the past). Furthermore, the pre-completion non-image medical data describes (in particular defines) for example at least one of a past treatment which the patient has undergone, his past and present medication and his reaction to previous treatment. The information contained in the pre-completion non-image medical data is linked with a point in time lying before completion of the medical procedure, i.e. before execution of the medical procedure on the anatomical structure has started or while it is being executed, but has not been finished yet.

The post-completion non-image medical data contains types information preferably corresponding to those contained in the pre-completion non-image medical data. However, the post-completion non-image medical data may also contain other (in particular, the same but less or more, but also different and/or less and/or more) types of information than the pre-completion non-image medical data. The information contained in the post-completion non-image medical data is linked with a point in time lying after completion of the medical procedure, i.e. after execution of the medical procedure on the anatomical structure has finished.

The pre-completion non-image medical data and the post-completion non-image medical data are stored preferably in a database, in particular a registry, so that they may be retrieved as required. The post-completion non-image medical data may be determined a plurality of times after the medical procedure has been completed, e.g. in order to generate registry-follow up to track the quality of the outcome at different points in time after the medical procedure has been completed.

The plan for execution described by the medical procedure planning data contains in particular information defining at least one of a dose distribution (in particular, spatial distribution of a dose of ionizing radiation e.g. for radiotherapy or radiosurgery), a geometry (in particular, at least one of shape and size, in particular of shape and volume) of tissue to be removed (in particular resected) and the time required to conduct the medical procedure, in particular a number of sessions for conducting the medical procedure (such as radiotherapy fractions or number of operations comprising open surgery). Furthermore, the medical procedure planning data may comprise information usable to adapt the plan for execution to information gathered during execution of the medical procedure, in particular to the pre-completion medical image data (e.g. in case the pre-completion medical mage data reveals that an unexpected event occurred during execution of the medical procedure which requires adaptation of the plan for execution).

The procedure application data is determined preferably as a combination of the pre-completion medical image data and the medical procedure planning data, for example the abstract information contained in the medical procedure planning data may be applied to the pre-completion medical image data so that a visual representation of a dose distribution is generated as an overlay on the visual representation of the anatomical structure. Alternatively, or additionally, the position of tissue to be removed (e.g. the position of a target region comprising a tumour which shall be irradiated with ionizing radiation) may be highlighted in the pre-completion medical image data to generate the procedure planning data. However, it is not necessary to generate an image view visible for humans from the pre-completion medical image data to determine the procedure planning data. It rather is sufficient to bring the information (e.g. positional information) into the same reference system used to define positions in the pre-completion medical image information. In particular, establishing a coordinate mapping between the medical procedure planning data and the pre-completion medical image data will suffice to properly apply the medical procedure planning data to the pre-completion medical image data and thereby determine the procedure application data.

In a preferred second embodiment, the quality measure describes (in particular defines) a measure of accuracy of in particular execution of the medical procedure or other medical quality issue, in particular treatment efficiency, associated with the medical procedure.

In the second embodiment, the measure of the accuracy is described (in particular defined) in particular by a value defining a geometric difference (in particular a difference in at least one of a size, in particular volume and a two-dimensional geometric quantity such as a distance, and a shape) between the procedure application data and the post-completion medical image data or by a statistical metric derived from the comparison of the pre-completion medical image data and the post-completion medical image data in regard of the of at least one of the pre-completion non-image medical data and the post-completion non-image medical data.

In a preferred third embodiment, the medical procedure can be any kind of medical procedure, in particular a medical procedure which encompasses at least one of therapy and surgery. For example, the medical procedure comprises at least one of radiotherapy, radiosurgery, an implantation procedure and a resection procedure.

In a preferred fourth embodiment, the outcome quality data is determined by comparing at least one of a geometry, in particular at least one of a size, in particular at least one of a volume and a two-dimensional geometric quantity, and shape, and metabolic activity of tumour tissue described by the procedure application data and the post-treatment medical image data.

In a preferred fifth embodiment, the outcome quality data is determined by determining a deviation, in particular a deviation of at least one of 1. an implantation trajectory, location or field of effect, and 2. a cavity, between the procedure application data and the post-completion medical image data.

In a preferred sixth embodiment, the method in accordance with the invention further comprises the following features:
 acquiring atlas data describing (in particular defining) an image-based model of the anatomical structure as a common reference system,
 wherein all available medical image data, in particular the pre-completion medical image data and the post-completion medical image data and the procedure application data, is linked across a plurality of patients to (in particular matched with) the common reference frame by applying an image fusion algorithm.

In particular, a spatial relationship (in particular at least one of position and orientation) of the aforementioned datasets relative to the common reference frame defined by the image-based model is determined as a result of the image fusion algorithm. The image fusion algorithm establishes a transformation (in particular, spatial transformation such as a coordinate mapping) between the datasets which are input into the algorithm. The transformation may also serve as a measure of similarity between the input datasets. The transformation is determined in particular by comparing the distribution of colour values (such as greyscale values, but also polychrome values can in general be processed) in each of the datasets (which all comprise image information). The distribution of colour values is in particular their spatial distribution and their neighbourhood relationships. Basically, specific pixels are determined to represent corresponding image information in datasets to be compared (i.e. input into the image fusion algorithm) (i.e. identical or similar to a predetermined degree, for example with a predetermined degree of probability) if they have a similar distribution of colour values around them in each of the datasets to be compared.

However, the colour value or colour values representing the anatomical structure depends or depend on the imaging modality applied for generating the respective image data describing the anatomical structure. Preferably, the atlas data is multi-modal atlas data which comprises image information generated by applying at least two imaging modalities. For example, the image based-model is defined by one dataset included in the atlas data which was generated by application of computed x-ray tomography, and one dataset included in the atlas data which was generated by application of magnetic resonance tomography. Thus, the atlas data may comprise the colour values for a plurality of imaging modalities, i.e. the image appearance of the image-based model is described (in particular defined) for a plurality of imaging modalities. This provides the advantage that medical image data (such as the pre-completion medical image data and the post-completion medical image data) which was generated with different imaging modalities (e.g. the pre-completion medical image data generated from a computed x-ray tomography, and the post-completion medical image data generated from a magnetic resonance tomography) may be matched with the common reference frame.

In preferred seventh embodiment, the method in accordance with the invention is executed for a plurality of patients and a quality measure is determined for each one of the patients, and preferably statistical quality data is determined based on the outcome quality data which has been determined for each patient of the plurality of patients, wherein the statistical quality data describes a statistical measure describing the plurality of quality measures.

In the seventh embodiment, the statistical measure is in particular a metric describing (in particular defining) the inference value, in particular at least one of reliability, validity and objectivity of the quality measures in terms of probability, for example statistical significance for multi-variate regression, statistical power for effect size calculation or sensitivity/specificity for a machine learning-based predictive method such as a Support Vector Machines. For example, the method in accordance with the invention may output as an intermediate or final result statistical information allowing a statement like "one specific hospital treats older patients suffering from prostate carcinoma using a specific radiotherapy approach with less accuracy than another specific hospital".

In the seventh embodiment, the plurality of patients comprises in particular patients which underwent the medical procedure at an executive medical entity which differs from the executive medical entity at which other ones of the plurality of patients underwent the medical procedure by being a different entity or by a time state of said entity. In the framework of this invention, the term of medical entity encompasses a medical institution such as a hospital or a care group, i.e. an enterprise operating a plurality of hospitals, or a single doctor's office), and medical personnel such as an individual medical practitioner (e.g. a physician or a medical physicist) or a group of medical practitioners. The time state is defined in particular as the point in time at which the medical procedure was executed by the specific medical entity or entities. This allows e.g. outputting as an intermediate or final result statistical information allowing a comparison of performance of medical entities over time.

In the seventh embodiment, the method in accordance with the invention further comprises in particular:
correlating at least one of the outcome quality data, the statistical quality data and the procedure application data with the pre-completion non-image medical data to determine a significant statistical measure describing a context between the additional characteristic and the at least one of the outcome quality data, the statistical quality data and the procedure application data.

In a preferred eighth embodiment, the pre-completion non-image medical data describes (in particular defines) in particular properties of the medical procedure and is acquired based on pre-completion medical image data, for example is extracted from the pre-completion medical image data by algorithmic means, or based on statistically associating geometric formations in the pre-completion medical image data with pre-completion non-image medical data describing at least one of the patient and the medical executive entity. For example, the pre-completion medical image data may be searched for an image region which corresponds to information contained in the pre-completion non-image medical data and vice versa (i.e. the pre-completion non-image medical data may be searched for information corresponding to a specific image region defined by the pre-completion medical image data). This may support determination whether e.g. whether a certain type on information contained in the pre-completion non-image medical data is at all applicable to the pre-completion medical image data.

In a preferred ninth embodiment, the above-described medical data processing method of determining an outcome quality of a medical procedure according to any one of the first to eighth embodiments is used for determining, based on the outcome quality data, entity performance data describing (in particular defining) a performance of a medical entity such as at least one of a medical institution, in particular a hospital or medical practice, and a medical practitioner, in particular a physician or medical physicist. The term of performance encompasses in particular the manner in which the medical entity has executed the medical procedure, more particularly the efficiency (in particular economic efficiency) of the medical entity for executing the medical procedure. Alternatively or additionally, the term of performance encompasses in particular the medical results (e.g. whether patient was cured or damage was inflicted upon the patient) achieved. The method in accordance with the invention also allows determining a performance as a combination, e.g. correlation, of the information describing (in particular defining) the efficiency and the achieved medical results.

In a second aspect, the invention is directed to a data processing method of using outcome quality data to inform a treatment planning procedure by automatically pre-setting default parameters of the treatment planning software according to the value of the quality measure, the method comprising execution of the above-described medical data processing method of determining an outcome quality of a medical procedure according to any one of the first to ninth embodiments to determine the outcome quality data.

In further aspects, the invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, in particular electrical, in particular technically generated) signal wave, in particular a digital signal wave, carrying information which represents the program, in particular the aforementioned program, which in particular comprises code means which are adapted to perform any or all of the method steps described herein.

In particular, the invention does not involve, comprise or encompass an invasive step which would represent a substantial physical interference with the body requiring professional medical expertise to be carried out and entailing a substantial health risk even when carried out with the required professional care and expertise. In particular, the invention does not involve, comprise or encompass any surgical or therapeutic activity. The invention is instead directed to a method usable for planning such a procedure. For this reason alone, no surgical or therapeutic activity and in particular no surgical or therapeutic step is necessitated or implied by carrying out the invention.

It is within the scope of the present invention to combine one or more features of one or more embodiments in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can in particular be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user.

One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, in particular handheld, device such as a smart phone or personal digital assistant or digital media player.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The atlas data preferably describes (in particular defines, more particularly represents and/or is) a general three-dimensional shape of the anatomical structure. The atlas data therefore represents an atlas of the anatomical body part. An atlas typically consists of a plurality of generic models of objects, wherein the generic models of the objects together form a complex structure. In particular, the atlas constitutes a statistical model of a patient's body (in particular, a part of the body) which has been generated from anatomic information gathered from a plurality of human bodies, in particular from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes in particular the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices in particular are used to generate the image data in apparatus-based imaging methods. The imaging methods are in particular used for medical diagnostics, to analyse the anatomical body in order to generate images which are described by the image data. The imaging methods are also in particular used to detect pathological changes in the human body. However, some of the changes in the anatomical structure, in particular the pathological changes in the structures (tissue), may not be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing" tumours, it is thought that approximately 10% of brain tumours are not discernible on a scan and are in particular not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change. In this application, the term "image morphing" is also used as an alternative to the term "elastic image fusion", but with the same meaning. Elastic fusion transformations (for example, elastic image fusion transformations) are in particular designed to enable a seamless transition from one dataset (for example a first dataset such as for example a first image) to another dataset (for example a second dataset such as for example a second image). The transformation is in particular designed such that one of the first and second datasets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field. These vectors are determined by the optimisation algorithm in such a way as to result in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). These constraints include in particular the constraint that the transformation is regular, which in particular means that a Jacobian determinant calculated from a matrix of the deformation field (in particular, the vector field) is larger than zero, and also the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used. In the steps of the optimisation algorithms, the voxels are in particular shifted by a magnitude in a direction such that the degree of similarity is increased. This magnitude is preferably less than a predefined limit, for instance less than one tenth or one hundredth or one thousandth of the diameter of the image, and in particular about equal to or less than the distance between neighbouring voxels. Large deformations can be implemented, in particular due to a high number of (iteration) steps. The determined elastic fusion transformation can in particular be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity. A measure of similarity can in particular be determined on the basis of a determined correlation between the first and second datasets.

DESCRIPTION OF THE FIGURES

In the following, the invention is described with reference to the enclosed Figures which represent preferred embodiments of the invention. The scope of the invention is not however limited to the specific features disclosed in the Figures, wherein

Figure 1:
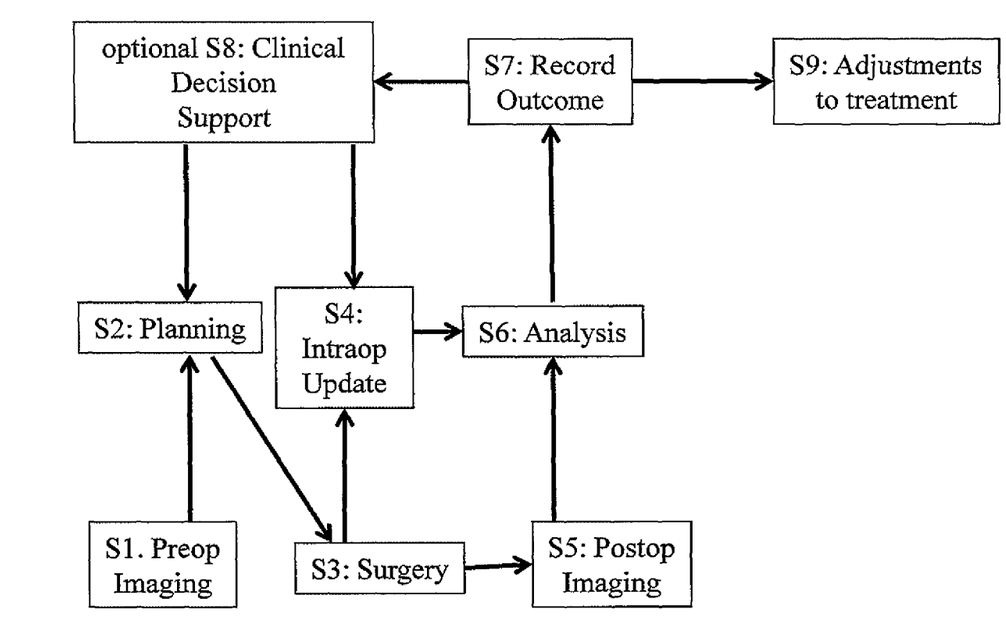
FIG. 1 is a flow diagram showing the steps of the method in accordance with the invention.

FIG. 1 shows the flow of steps of the method in accordance with the invention according to a preferred embodiment. The invention is not to be construed as being limited to the steps shown in FIG. 1.

In step S1, the pre-completion medical image data is acquired by pre-operative ("preop") imaging of the anatomical structure. Along with the pre-completion medical image data the pre-completion non-image medical data is acquired. This serves as basis for acquiring the medical procedure planning data and the procedure application data in step S2. The method then continues with step S3 which relates to conducting (executing) the medical procedure which may encompass surgery, e.g. an implantation surgery. In subsequent optional step S4, a possible intra-operative ("intraop") update of the pre-completion medical image data are acquired by repeating the imaging while the medical procedure is being executed. In step S5, the post-completion medical image data is acquired (along with the post-completion non-image medical data) is acquired after the medical procedure has been completed (i.e. post-operatively/ "postop"). The data acquired and determined in steps S1 to S5 is analysed in step S6, e.g. by applying a statistical algorithm to determine and record the quality of the outcome (embodied by for example an accuracy) in step S7. Preferably, the quality of the outcome is recorded only if it reaches a predetermined level, in particular a predetermined level indicating that execution of the medical procedure was successful from a medical point of view. The thus-determined quality of the outcome can be optionally used for future clinical decision support in a feedback loop included in step S8, i.e. the quality of the outcome may serve as a basis for planning a future medical procedure or may serve as a basis to decide whether step S4 needs to be executed. The quality of the outcome may also serve as a basis for adjusting the medical procedure (treatment) in step S9, for example to change the way of conducting the implantation surgery to achieve better medical results and/or increase efficiency.

Advantages and advantageous features of the method in accordance with the invention are in particular:

I. On the Side of the Patient:
personalized health care
continuous information pre- & postop
patient community
decision support
patient can provide feedback II. On the Side of the Physician:
optimal outcomes
direct application of evidence based medicine/treatment justification
clinical decision support
health
value measurement
performance metrics III. On the Side of an Implant Distributor:
feedback of implant efficacy in the field from multiple sources of information
continuous care for the implant
unique health value measurement using imaging-based outcome data while competition implements basic version IV. On the Side of Hospital:
treatment and physician efficiency are recorded
health value measurement

The invention claimed is:

1. A computer implemented image processing method for the assessment of medical procedures, comprising:
acquiring pre-completion medical image data describing an anatomical structure of a patient's body in a state before the medical procedure has been completed on the anatomical structure, the anatomical structure being subject to the medical procedure;
the medical procedure being at least one of radiotherapy or radiosurgery procedure;
acquiring pre-completion non-image medical data describing a state and medical history of the patient before the medical procedure has been completed on the anatomical structure;
acquiring medical procedure planning data describing a plan for execution of the medical procedure to be carried out on the anatomical structure;
determining, based on the pre-completion medical image data and the medical procedure planning data, procedure application data describing an application of the medical procedure planning data to the pre-completion medical image data, wherein determining the procedure application data comprises establishing a coordinate mapping between the medical procedure planning data and the pre-completion medical image data;
acquiring atlas data describing an image-based model of the anatomical structure as a common reference frame, wherein the atlas data is multi-modal;
linking available medical image data, including the pre-completion medical image data and the procedure application data, across a plurality of patients to the common reference frame by applying an image fusion algorithm;
establishing, by the image fusion algorithm, a transformation between a common reference frame of the atlas data and the pre-completion medical image data and the procedure application data by applying the image fusion to the atlas data, pre-completion medical image data and the procedure application data;
wherein the transformation provides a measure of similarity between the atlas data and the pre-completion medical image data and the procedure application data by comparing the distribution of color values in each of the atlas data, pre-completion medical image data and procedure application data;
creating a visual representation of a dose distribution for the radiotherapy or radiosurgery generated as an overlay on the anatomical structure to at least partially generate the procedure planning data;
applying at least the procedure application data to the radiosurgery or radiotherapy procedure;
acquiring post-completion non-image medical data describing a state and medical history of the patient after the medical procedure has been completed on the anatomical structure;
acquiring post-completion medical image data describing the anatomical structure in a state after the medical procedure has been completed on the anatomical structure;
applying the transformation to the post-completion medical image data;
determining, based on the procedure application data and the pre-completion non-image medical data and the post-completion non-image medical data and the post-completion medical image data, outcome quality data comprising a quality measure describing a quality of the outcome of the medical procedure, wherein the quality measure describes a measure of accuracy of execution of the medical procedure, wherein the measure of accuracy is described by a value defining a geometric difference between the procedure application data and the post-completion medical image data;
modifying the procedure planning data based upon the outcome quality data.

2. A computer implemented image processing method for determining an outcome quality of a medical procedure, comprising:
- acquiring pre-completion medical image data describing an anatomical structure of a patient's body in a state before the medical procedure has been completed on the anatomical structure, the anatomical structure being subject to the medical procedure;
- the medical procedure being at least one of radiotherapy or radiosurgery procedure;
- acquiring pre-completion non-image medical data describing a state and medical history of the patient before the medical procedure has been completed on the anatomical structure;
- acquiring medical procedure planning data describing a plan for execution of the medical procedure to be carried out on the anatomical structure;
- determining, based on the pre-completion medical image data and the medical procedure planning data, procedure application data describing an application of the medical procedure planning data to the pre-completion medical image data, wherein determining the procedure application data comprises establishing a coordinate mapping between the medical procedure planning data and the pre-completion medical image data;
- establishing, by an image fusion algorithm, a transformation between a common reference frame of atlas data and the pre-completion medical image data and the procedure application data by applying the image fusion to the atlas data, pre-completion medical image data and the procedure application data;
- wherein the transformation provides a measure of similarity between the atlas data and the pre-completion medical image data and the procedure application data by comparing the distribution of color values in each of the atlas data, pre-completion medical image data and procedure application data;
- creating a visual representation of a dose distribution for the radiotherapy or radiosurgery generated as an overlay on the anatomical structure to at least partially generate the procedure planning data;
- acquiring post-completion non-image medical data describing a state and medical history of the patient after the medical procedure has been completed on the anatomical structure;
- acquiring post-completion medical image data describing the anatomical structure in a state after the medical procedure has been completed on the anatomical structure;
- applying the transformation to the post-completion medical image data;
- determining, based on the procedure application data and the pre-completion non-image medical data and the post-completion non-image medical data and the post-completion medical image data, outcome quality data comprising a quality measure describing a quality of the outcome of the medical procedure;
- wherein the quality measure describes a measure of accuracy of execution of the medical procedure;
- wherein the measure of accuracy is described by a value defining a geometric difference between the procedure application data and the post-completion medical image data.

3. The method according to claim 2, wherein the measure of the accuracy is described by a statistical metric derived from the comparison of the pre-completion medical image data and the post-completion medical image data in regard of the of at least one of the pre-completion non-image medical data and the post-completion non-image medical data.

4. The method according to claim 2, wherein the outcome quality data is determined by comparing at least one of a geometry, in particular at least one of a size, in particular volume, and shape, and metabolic activity, of tumour tissue described by the procedure application data and the post-treatment medical image data.

5. The method according to claim 2, wherein the outcome quality data is determined by determining a deviation, in particular a deviation of at least one of an implantation trajectory, location or field of effect and a cavity between the procedure application data and the post-completion medical image data.

6. The method according to claim 2, wherein the method is executed for a plurality of patients and a quality measure is determined for each one of the patients, and wherein statistical quality data is determined based on the outcome quality data determined for each patient of the plurality of patients, wherein the statistical quality data describes a statistical measure describing the plurality of quality measures.

7. The method according to claim 6, wherein the statistical measure is a metric describing the inference value, in particular at least one of reliability, validity and objectivity of the quality measures in terms of statistical significance for multivariate regression, statistical power for effect size calculation or sensitivity or specificity for a machine learning-based predictive method.

8. The method according to claim 7, wherein the pre-completion non-image medical data describes properties of the medical procedure and is extracted from the pre-completion medical image data by algorithmic means, or based on statistically associating geometric formations in the pre-completion medical image data with pre-completion non-image medical data describing at least one of the patient and the medical executive entity.

9. The method according to claim 6, further comprising:
- correlating at least one of the outcome quality data, the statistical quality data and the procedure application data with the pre-completion non-image medical data to determine a significant statistical measure describing a context between the additional characteristic and the at least one of the outcome quality data, the statistical quality data and the procedure application data.

* * * * *